United States Patent [19]

Bey et al.

[11] 4,353,828

[45] Oct. 12, 1982

[54] PREPARATION OF FLUORINATED METHYL AMINOALKANOIC ACIDS AND NOVEL PROCESS INTERMEDIATES

[75] Inventors: Philippe Bey, Strasbourg, France; Fritz Gerhart, Willstaett, Fed. Rep. of Germany; Viviane Van Dorsselaer, Strasbourg, France

[73] Assignee: Merrell Toraude et Compagnie, Strasbourg, France

[21] Appl. No.: 170,395

[22] Filed: Jul. 21, 1980

[30] Foreign Application Priority Data

Jul. 26, 1979 [GB] United Kingdom ............... 7926030
Jan. 25, 1980 [GB] United Kingdom ............... 8002554

[51] Int. Cl.$^3$ ............... C07C 87/26; C07D 209/48
[52] U.S. Cl. ............... 260/326 NS; 560/161; 564/90; 564/187; 564/215; 564/279; 564/509
[58] Field of Search ............... 564/509, 187, 180, 90, 564/156, 215; 560/137, 161; 562/442; 260/326 NS

[56] References Cited

U.S. PATENT DOCUMENTS 3,320,277  5/1967  Mehta et al. ............... 564/509
3,478,100 11/1969  Gale ............... 564/509

*Primary Examiner*—Natalie Trousof
*Assistant Examiner*—L. Hendriksen
*Attorney, Agent, or Firm*—David E. Frankhouser; William J. Stein

[57] ABSTRACT

Fluorinated alkenylamines of the Formula V

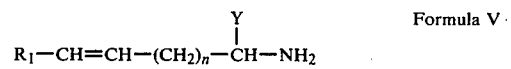

Formula V wherein n represents 0, 1, 2 or 3; $R_1$ represents hydrogen or $C_1$–$C_{10}$ alkyl and Y represents (a), when n represents 0, $CH_2F$, (b), when n represents 1, $CH_2F$ or $CHF_2$, or (c) when n represents 2 or 3, $CH_2F$, $CHF_2$ or $CF_3$ are novel process intermediates. They are obtained by hydrolysis and subsequent reduction of the corresponding alkenyl fluorinated methyl ketimine magnesium halides, which are novel compounds resulting from reaction of the corresponding alkenyl magnesium halides with the corresponding fluorinated acetonitriles. The fluorinated alkenylamines of Formula V are oxidized while the amino group is protected to provide, after removal of the amine protecting group, the corresponding fluorinated methyl aminoalkanoic acids which are useful pharmacological or anti-bacterial agents.

5 Claims, No Drawings

PREPARATION OF FLUORINATED METHYL AMINOALKANOIC ACIDS AND NOVEL PROCESS INTERMEDIATES

FIELD OF INVENTION

The present invention relates to fluorinated methyl aminoalkanoic acids and provides a novel process for the preparation thereof and novel intermediates in said process.

BACKGROUND OF INVENTION

Fluorinated methyl aminoalkanoic acids of the Formula I

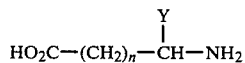     Formula I wherein
n represents 0, 1, 2 or 3 and
Y represents:
(a), when n represents 0, $CH_2F$,
(b), when n represents 1, $CH_2F$ or $CHF_2$, and
(c), when n represents 2 or 3, $CH_2F$, $CHF_2$ or $CF_3$
are, in general, useful as pharmacological or antibacterial agents.

Fluorinated methyl γ-aminobutyric and δ-aminopentanoic acids of the Formula VI

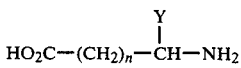     Formula VI wherein
n represents 2 or 3; and
Y represents $CH_2F$, $CHF_2$ or $CF_3$ and pharmacologically acceptable acid addition salts and certain derivatives of said acids of Formula VI are useful pharmacological agents, in particular as γ-aminobutyric acid transaminase ("GABA-T") inhibitors (see U.K. Patent Specification No. 2005264 A).

γ-Monofluoromethyl-γ-aminobutyric acid of Formula VIII

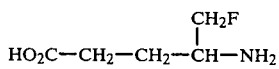     Formula VIII and pharmacologically acceptable salts are also reported to be glutamic acid decarboxylase inhibitors (see European Patent Specification No. 78100059.1).

β-Monofluoro-α-aminopropionic acids (i.e. 3-fluoro alanines of the Formula IX)

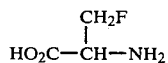     Formula IX and pharmacologically acceptable salts are useful antibacterial agents (see U.K. Patent Specification No. 1367674). Compounds of Formula IX having the D-configuration are useful pharmacological anti-bacterial agents and 2-deutero-3-fluoro-D-alanine is particularly preferred for this purpose (see also U.K. Patent Specification No. 1367674).

It has recently been found that β-fluorinated methyl β-aminopropionic acids of the Formula VII

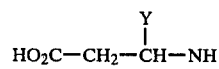     Formula VII wherein Y represents $CH_2F$ or $CHF_2$ and certain derivatives thereof are novel and useful pharmacological agents, in particular GABA-T inhibitors. The derivatives are the pharmaceutically acceptable esters and amides derived from the acid group, amides and urethanes derived from the amine group, lactams and salts. The preferred compounds are those of the Formula VIIa

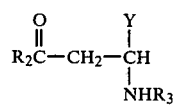     Formula VIIa wherein
Y represents $CH_2F$ or $CHF_2$;
$R_2$ represents $C_1$-$C_8$ alkyl, -$NR_4R_5$ (wherein each of $R_4$ and $R_5$ is hydrogen or $C_1$-$C_4$ alkyl or an aminocarboxylic acid residue derived by removal of a hydrogen atom from the amino moiety of an L-aminocarboxylic acid; and $R_3$ is hydrogen, $C_2$-$C_5$ alkylcarbonyl, $C_2$-$C_5$ alkoxycarbonyl, phenyl-($C_1$-$C_4$ alkyl)carbonyl, phenyl ($C_1$-$C_4$ alkoxy)carbonyl, phenylcarbonyl, phenoxycarbonyl or an aminocarboxylic acid residue derived by removal of an hydroxy group from the carboxy moiety of an L-aminocarboxylic acid; and the lactams thereof wherein $R_3$ is hydrogen, and pharmacologically acceptable salts thereof.

It is an object of the present invention to provide a new and useful process for preparing fluorinated methyl aminoalkanoic acids of Formula I.

It is a particular, but not exclusive, object of the present invention to provide a new and useful process for preparing fluorinated alanines of the Formula IX.

It is an especial object of the present invention to provide a new and useful process for preparing 2-deutero-3-fluoro-D-alanine.

SUMMARY OF INVENTION

It has been found that fluorinated methyl aminoalkanoic acids of Formula I can readily be prepared from a corresponding alkenyl magnesium halide of the Formula II:

$$R_1-CH=CH-(CH_2)_n-MgX \qquad II$$

wherein:
$R_1$ represents hydrogen or a $C_1$-$C_{10}$ alkyl group;
n represents 0, 1, 2 or 3; and
X represents bromine, chlorine or iodine, and a fluorinated acetonitrile of the Formula III $$YCN \qquad III$$

wherein Y is as defined above in connection with Formula I. The reaction product of said reactants is a novel alkenyl fluorinated methyl ketimine magnesium halide of the Formula IV

Formula IV wherein $R_1$, n and X are as defined in connection with Formula II and Y is as defined in connection with Formula I, which is hydrolysed and then reduced to a novel fluorinated alkenylamine of Formula V. The fluorinated alkenylamine is oxidized whilst the amino group is protected and subsequently the amino group is freed to yield the desired acid of Formula I.

The said process also can be used to prepare the analogues of the fluorinated methyl aminoalkanoic acids of Formula I in which Y represents $CHF_2$ or $CF_3$ when n represents 0 and Y represents $CF_3$ when n represents 1. However, no utility for said analogues is known to us.

DETAILED DESCRIPTION OF THE INVENTION

The alkenyl magnesium halides of Formula II are generally known and can readily be prepared in manner known per se for making Grignard reagents from the corresponding alkenyl halides of Formula X

    X wherein $R_1$ and n are as defined in connection with Formula IV; and X' represents bromine, iodine or, when $R_1$ represents hydrogen, chlorine by contacting with magnesium, for example magnesium in the form of turnings, in an appropriate solvent suitable for Grignard-type solutions, for example an ether, e.g. tetrahydrofuran, diethylether and the like and mixtures thereof. Preferably, the reaction is carried out under an inert atmosphere such as, for example nitrogen, argon and the like. In particular, the halide of Formula X can be added very slowly to magnesium turnings in tetrahydrofuran under a nitrogen atmosphere or in diethylether and the reaction allowed to proceed for from 30 minutes to 24 hours at a temperature of from about $-20°$ C. to $70°$ C., preferably from about $25°$ C. to the boiling point of the solvent. At the beginning of the reaction, a trace of methyl iodide is added.

In an alternative process known per se for making Grignard reagents, the alkenyl magnesium halides of Formula II are prepared by contacting in a suitable solvent such as, for example, tetrahydrofuran (THF) and TRAPP mixture (THF/petroleum ether/diethylether) the corresponding alkenyl bromide or iodide of the Formula Xa

    Xa wherein $R_1$ and n are as defined in connection with Formula IV; and X" represents bromine or iodine with an alkyl lithium of the Formula XI R'Li    XI wherein R' represents lower alkyl to form an alkenyl lithium of the Formula XII

    XII wherein $R_1$ and n are as defined in connection with Formula IV and subsequently contacting without separation from the reacted mixture said alkenyl lithium with a magnesium halide of the Formula XIII MgX    XIII wherein X represents bromine, chlorine or iodine to yield the desired alkenyl magnesium halide. Preferably R' represents sec or, especially, tert butyl and the second of the aforementioned process steps is carried out at a temperature between $15°$ C. and the boiling point of the solvent.

$R_1$ in Formula IV represents hydrogen or any straight or branched chain alkyl group of from 1 to 10 carbon atoms, especially from 1 to 4 carbon atoms. Illustrative of alkyl groups of from 1 to 10 carbon atoms are methyl, ethyl, n-propyl, isopropyl, n-butyl, tert-butyl, n-pentyl, n-hexyl, isohexyl, n-heptyl, n-octyl, n-nonyl, n-decyl and the like. Reference in this specification (including the Claims thereof) to a specific alkyl group or moiety having structural isomers includes all of these isomers and mixtures thereof unless a particular isomer is specified or clearly implied by the context. It is particularly preferred that $R_1$ represents hydrogen or methyl.

n in Formula IV represents zero, 1, 2 or 3. The value of n will be determined by the required fluorinated methyl aminoalkanoic acid of Formula I to be prepared. Thus, (a) n will be zero when a fluorinated methyl aminoacetic acid of Formula I is required; (b) n will be 1 when a fluorinated methyl aminopropionic acid of Formula I is required; (c) n will be 2 when a fluorinated methyl aminobutyric acid of Formula I is required; and (d) n will be 3 when a fluorinated methyl aminopentanoic acid of Formula I is required.

X in Formula IV represents bromine, chlorine or iodine with chlorine and, especially, bromine being preferred.

Y in Formula IV represents monofluoromethyl ($CH_2F$), difluoromethyl ($CHF_2$) or trifluoromethyl ($CF_3$) and will be chosen having regard to the required fluorinated methyl aminoalkanoic acid of Formula I to be prepared. Thus, (a) Y will represent $CH_2F$ when a monofluoromethyl aminoalkanoic acid of Formula I is required; (b) Y will represent $CHF_2$ when a difluoromethyl aminoalkanoic acid of Formula I is required; and (c) Y will represent $CF_3$ when a trifluoromethyl aminoalkanoic acid of Formula I is required. Having regard to the presently known pharmacological preferences for fluorinated methyl aminoalkanoic acids, it is generally preferred that Y represents $CH_2F$ or $CHF_2$.

The atom or group represented by $R_1$, the atom represented by X and the value of n in other formulae in this specification will, unless otherwise stated, correspond to those of Formula IV supra. In this connection all ranges given in this specification (including the Claims thereof) are inclusive of the specified lower and upper limits. Thus, for example the ranges 1 to 10 carbon atoms, 30 minutes to 24 hours and $-20°$ C. to $70°$ C. referred to above include respectively 1 and 10 carbon atoms, 30 minutes and 24 hours, $-20°$ C. and $70°$ C. Further, references to compounds having optical isomers include the individual isomers, racemates and other optical isomer mixtures thereof unless a particular isomer is specified or clearly implied by the context. Moreover, reference to an atom includes isotopes thereof unless a particular isotope is specified or clearly implied by the context. Also, the term "lower" used in contexts indicating the carbon content of a group means having 1 to 6 (inclusive) carbon atoms.

The alkenyl magnesium halides of Formula II usually will be used without separation from the solution in which they are formed but after removal of any excess magnesium. A fluorinated acetonitrile of Formula III can be added to said solution as a solution in a suitable aprotic solvent such as for example an ether, e.g. tetrahydrofuran, diethylether, dimethoxyethane, dimethoxymethane and the like; aromatic hydrocarbon, e.g. benzene, toluene, xylene and the like; and mixtures of two or more thereof. Alternatively, in the case of monofluoroacetonitrile, it can be added without a solvent whilst in the cases of difluoroacetonitrile and trifluoroacetonitrile, they can be added as a gas. Suitably, the fluorinated acetonitrile is added at a molar ratio of from 0.5 to 1.2. The reaction mixture conveniently is maintained at a temperature of from $-78°$ C. to $0°$ C., preferably below $-20°$ C. and especially of from $-20°$ C. to $-30°$ C. The reaction time can vary from 10 minutes to 24 hours, preferably 10 minutes to 1 hour.

The reaction product of the reaction between the alkenyl magnesium halide and the fluorinated acetonitrile is an alkenyl fluorinated methyl ketimine magnesium halide of the Formula IV. These ketimine salts, which decompose above $-10°$ C., are believed to be novel compounds and hence the invention includes said salts per se. Usually, they will be used without separation from the reacted mixture but, if desired, can be isolated by evaporating off the solvent under vacuum at a temperature below $-10°$ C., preferably below $-30°$ C. or by lyophilization (i.e. freeze drying).

According to one preferred embodiment of the first aspect of the present invention, there are provided allyl mono- and di-fluoromethyl ketimine magnesium halides of the Formulae IVa and IVb

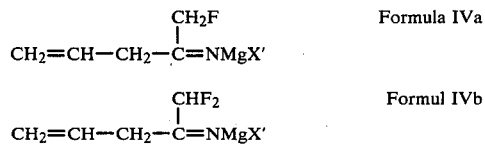

wherein

X' represents chlorine or, especially, bromine.

According to a further and especially preferred embodiment of the first aspect of the present invention, there are provided 1-alkenyl fluorinated methyl ketimine magnesium halides of the Formula IVc

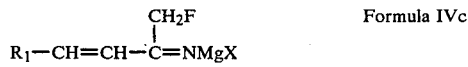

wherein $R_1$ represents hydrogen or a straight or branched chain alkyl group of from 1 to 10, preferably 1 to 6, carbon atoms, preferably methyl or, especially, hydrogen; and X represents bromine, chlorine or iodine, preferably chlorine and, especially, bromine.

Particularly preferred ketimine salts of Formula IVc are those of Formula IVd and IVe

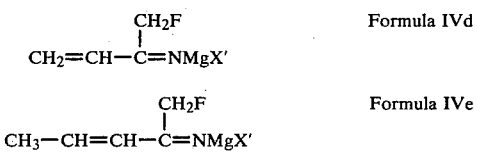

wherein

X' represents chlorine or, especially, bromine.

Specific examples of ketimine salts of Formula IV include:

vinyl monofluoromethyl ketimine magnesium bromide;

allyl difluoromethylketimine magnesium bromide;

vinyl monofluoromethyl ketimine magnesium chloride;

allyl difluoromethyl ketimine magnesium chloride;

1-propenyl monofluoromethyl ketimine magnesium bromide; allyl monofluoromethyl ketimine magnesium bromide;

2-butenyl monofluoromethyl ketimine magnesium bromide;

2-butenyl difluoromethyl ketimine magnesium bromide;

3-butenyl monofluoromethyl ketimine magnesium bromide;

3-butenyl difluoromethyl ketimine magnesium bromide;

4-pentenyl monofluoromethyl ketimine magnesium bromide;

4-pentenyl difluoromethyl ketimine magnesium bromide;

3-pentenyl difluoromethyl ketimine magnesium bromide;

4-hexenyl monofluoromethyl ketimine magnesium bromide;

3-butenyl-trifluoromethyl ketimine magnesium bromide;

4-pentenyl-trifluoromethyl ketimine magnesium bromide;

3-pentenyl-trifluoromethyl ketimine magnesium bromide.

The ketimine salts of Formula IV can be hydrolysed and then reduced to corresponding fluorinated alkenylamines of Formula V. The hydrolysis usually will be carried out with a protic solvent, such as, for example water, a lower alkanol, especially methanol, and an aqueous lower alkanol, especially aqueous methanol. However, other hydrolysis conditions can be employed especially addition of an equimolar amount of an acid using a protic or aprotic solvent. Suitable acids include lower alkanoic acids, for example acetic and propionic acids and the like, aromatic carboxylic acids, for example benzoic acid and the like, and mineral acids, for example hydrochloric acid and the like. Conveniently, the reduction is carried out with a reducing agent which is a reducing hydride, such as, for example a borohydride, lithium aluminium hydride diborane, mixed complex hydride and the like.

Preferably, the borohydride is an alkali metal borohydride or cyanoborohydride, especially sodium borohydride, potassium borohydride, sodium cyanoborohydride or lithium borohydride. The borohydride reduction usually will be carried out in a protic solvent which serves to hydrolyse the ketimine salt. Suitable solvents include water; lower alkanols, e.g. methanol, ethanol and the like; and aqueous lower alkanols, e.g. aqueous methanol, aqueous ethanol and the like.

When lithium aluminium hydride, diborane or mixed complex hydride is used, the hydrolysis usually will be carried out as a separate first step using an equimolar amount of an acid in an aprotic solvent and then the hydride is added to the hydrolysis product without isolation from said solvent. Suitable aprotic solvents include ethers, for example diethylether, tetrahydrofuran, dimethoxyethane, and the like, aromatic hydrocarbons for example benzene, toluene, xylene and the like, and aliphatic hydrocarbons for example pentane, hexane and the like.

Conveniently, the ketimine salt solution is poured into a solution of the hydride reducing agent in said protic or aprotic solvent respectively at a temperature of about $-20°$ C. to $25°$ C. and the reaction permitted to proceed for about 1 to 20 hours. Preferably, a borohydride reducing agent is used.

The fluorinated alkenylamines of Formula V conveniently are separated from the reduction mixture and purified in the form of acid addition salts with mineral acids such as, for example, hydrochloric acid, hydrobromic acid and the like.

The fluorinated alkenylamines of Formula V can readily be converted in manner known per se into desired acid addition salts and the acid addition salts of said alkenylamines can readily be converted in manner known per se into the free alkenylamine or into other acid addition salts.

In the case of 1-alkenyl fluorinated methyl ketimine magnesium halides of Formula IV (n represents zero), it is surprising that the reduction takes place essentially selectively to yield the corresponding fluorinated 1-alkenylamine of Formula V because of the conjugated double bonds in the ketimine salt. The regioselectivity of the reduction in this case is an unexpected and significant advance in the art which permits the ready preparation of fluorinated alanines.

If it is desired to prepare a compound of Formula I in which there is a deuterium atom on the $\alpha$ carbon atom relative to the amino group, e.g. 2-deutero-3-fluoro-D-alanine, the reduction of the ketimine salt can be carried out with a deuteride reducing agent, e.g. sodium borodeuteride.

It is believed that the fluorinated alkenylamines of Formula V are novel compounds and hence the invention includes these amines and their acid addition salts per se.

According to one preferred embodiment of the third aspect of the present invention, there are provided 1-fluoro- and 1,1-difluoro-2-amino-4-pentenes of the Formula Vb and Vc

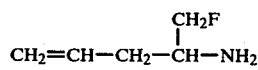
Formula Vb

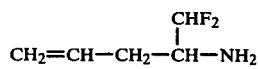
Formula Vc and acid addition salts thereof.

According to a further and especially preferred embodiment of the third aspect of the present invention, there are provided 1-fluorinated-2-aminoalkenes of Formula Vd

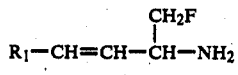
Formula Vd wherein
$R_1$ represents hydrogen or a straight or branched chain alkyl group of from 1 to 10 carbon atoms, preferably methyl or, especially, hydrogen; and acid addition salts thereof.

Particularly preferred 1-fluorinated-2-aminoalkene of Formula Vd is that of Formula Ve.

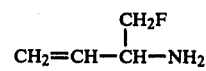
Formula Ve

Specific examples of fluorinated alkenylamines of Formula V include those corresponding to the exemplified ketimine salts of Formula IV, for example
1-fluoro-2-amino-3-butene;
1-fluoro-2-amino-3-pentene;
1-fluoro-2-amino-4-pentene;
1,1-difluoro-2-amino-4-pentene;
1-fluoro-2-amino-5-hexene;
1,1-difluoro-2-amino-6-heptene;
1,1-difluoro-2-amino-5-hexane;
1,1,1-trifluoro-2-amino-5-hexene;
1-fluoro-2-amino-7-octene, and the like.

Fluorinated methyl aminoalkanoic acids of Formula I can be prepared by oxidation of the corresponding fluorinated alkenylamine of Formula V in which the amino group is protected by a suitable blocking group to form the corresponding fluorinated methyl (protected amino) alkanoic acid and subsequently removing the blocking group in manner known per se to free the amino group or form an acid addition salt thereof. These reaction steps can be represented as follows:

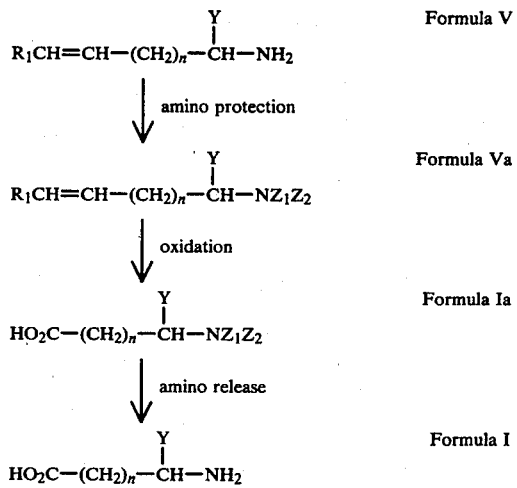

In the Formulae Va and Ia $R_1$ and n are as defined above in connection with Formula V and $Z_1$ is hydrogen and $Z_2$ is the blocking group or $Z_1$ and $Z_2$ together represent the blocking group or groups.

The blocking group suitably can be acyl, for example lower alkanoyl, e.g. acetyl, propionyl, trifluoroacetyl, and the like, aroyl, e.g. benzoyl, toluoyl and the like, lower alkoxycarbonyl, for example methoxycarbonyl, ethoxycarbonyl and the like, carbobenzoxy, benzenesulfonyl and tosyl and preferably is tert-butoxycarbonyl or benzenesulfonyl. Both amino hydrogen atoms can be substituted by a single blocking group such as, for example phthalyl and the like. The blocking groups are introduced in manner known per se by, for example, reaction of the amine with a lower alkanoyl or aroyl chloride, anhydride, sulfonylchloride, or tert-butyloxycarbonyloxyimino-2-phenylacetonitrile (BOC-ON). The preferred blocking groups tert-butoxycarbonyl and benzenesulfonyl are introduced with BOC-ON and benzenesulfonylchloride, respectively, in the presence of a base.

Suitably, the oxidation can be carried out using an oxidising agent such as, for example potassium permanganate, manganese dioxide, chromium trioxide, potassium dichromate, osmium tetroxide, ruthenium tetroxide and the like in a suitable solvent such as water, acetic acid, ethanol, acetone, pyridine, carbon tetrachloride, methylene chloride, diethylether, benzene, cyclohexane and the like. The oxidation can be performed at a temperature in the range 0° C. to the boiling point of the respective solvent and for a period in the range 5 minutes to 48 hours. Preferably, the oxidation is carried out with potassium permanganate in aqueous acetic acid at room temperature overnight.

The fluorinated-methyl-protected aminoalkanoic acids of Formula Ia can be isolated from the oxidation reaction product by removal of the solvent under vacuum followed by addition of water and extraction with ether or chloroform.

Removal of the blocking group after the oxidation step is performed in manner known per se for the relevant blocking group. Usually, said removal will be by hydrolytic cleavage using a strong organic or mineral acid such as, for example, trifluoroacetic acid, hydrochloric acid and the like acids; by catalytic hydrogenation using Pd or Pt catalyst; or by hydrogen chloride gas. Solvents can be used dependent upon the nature of the blocking group removal. For example, alcohols such as, for example, lower alkanols, e.g. methanol, ethanol and the like can be used for hydrogenation and an ether such as, for example, diethylether and the like for cleavage using hydrogen chloride gas. Reaction temperatures may vary from 0° C. to the boiling point of the respective solvent and reaction times from 10 minutes to 48 hours. The preferred procedure when tert-butoxycarbonyl is the blocking group is to saturate a diethylether solution with hydrogen chloride and leave overnight (i.e. about 16 hours) at room temperature to yield the aminoacid hydrochloride which can be purified by dissolving in ethanol and adding sufficient diethylether to recrystallize the aminoacid hydrochloride. The hydrochloride salt can readily be neutralized to provide the free aminoacid which can be treated in conventional manner to form other acid addition salts and base salts.

Optical resolution can be carried out in manner known per se on the aminoalkanoic acids of Formula I or, preferably, on the alkenylamines of Formula V. In the case of said acids, resolution usually will be with an optically active acid or base which forms a salt with respectively the amine or acid group of respectively a carboxy-protected or amino-protected derivative of the aminoalkanoic acid (see, for example, U.K. Patent Specification No. 1,389,859). In the case of said amines, resolution usually will be with an optically active acid which forms a salt or amide with the amine group. The desired isomer will be liberated by treatment in manner known per se of the resolved salt or amide. The "carboxy-protected" derivative can be, for example, an amide, nitrile ester and the like derivative and the "amino-protected" derivative can be, for example, a monoacylate, diacylate, alkylate or aralkylate, urethane and the like derivative. The optically active salts can be separated by fractional crystallization from a suitable solvent, such as, for example, a lower alkanol, e.g. methanol, ethanol and the like.

Suitable optically active acids for forming an acid addition salt with the alkenylamines of Formula V include the (+) and (−) isomers of tartaric, binaphthylphosphoric, malic, mandelic, camphorsulfonic, α-bromo-camphor-π-sulfonic and the like acids. The acid addition salt optical isomers can be separated by fractional crystallization from a suitable solvent, such as, for example, a lower alkanol, e.g. methanol, ethanol and the like.

Suitable optically active acids for forming amides with the alkenylamines of Formula V include the (+) and (−) isomers of 2-phenylpropionic, 2-phenylbutyric, 2-phenyl-3,3-dimethylbutyric, 2-phenyl-3-acetoxy-propionic and the like acids. The amide optical isomers can be separated by high pressure liquid chromatography.

The invention is illustrated in the following non-limiting Examples.

EXAMPLE 1

Allyl Monofluoromethyl Ketimine Magnesium Bromide

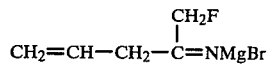

Allyl magnesium bromide is prepared under an atmosphere of nitrogen from 4.86 g (200 mmoles) magnesium turnings, allyl bromide (12.1 g, 100 mmoles) and dry ether (100 ml). The resultant allyl magnesium bromide Grignard solution is separated from the excess magnesium, cooled to −20° C., and fluoroacetonitrile (5.31 g, 90 mmoles) in ether (50 ml) is added, dropwise, during about 30 minutes. A gummy pale-grey precipitate of allyl monofluoromethyl ketimine magnesium bromide is formed which is used in Example 2 without separation from the solution but after stirring at −20° C. for a further 30 minutes.

EXAMPLE 2

1-Fluoro-2-Amino-4-Pentene

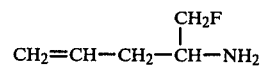

(A) The ketimine salt precipitate in solution from Example 1 at −20° C. is poured into a stirred mixture of methanol (200 ml), water (4 ml), and sodium borohydride (3.8 g, 100 mmoles) cooled to −40° C. The transfer of the gummy precipitate is facilitated by rinsing the reaction flask with 200 ml of cold dry tetrahydrofuran. After stirring for 1 hour at −20° C. and 30 minutes at 0° C., the mixture is acidified with 3 N hydrochloric acid (about 50 ml) and evaporated. Water is added to the residue and the resultant mixture (which is acidic) is extracted twice with ether to remove non-basic by-products, made alkaline with 4 N sodium hydroxide and extracted twice with ether again to yield free 1-fluoro- 2-amino-4-pentene in solution. After drying with sodium sulfate, dry hydrogen chloride gas is bubbled through the solution to form an oily precipitate (8.9 g) which is recrystallized from methanol by addition of diethylether to yield 1-fluoro-2-amino-4-pentene hydrochloride (6.8 g, 49%, mp. 124° C.).

Anal. Calcd. for $C_5H_{11}NFCl$: C, 43.02; H, 7.94; N, 10.03; Found: C, 43.28; H, 7.83; N, 9.81.

NMR ($D_2O$): δ2.50 (2H,t, J=7 Hz), 3.70 (1H, m), 4.50 (2H, d of m, $J_{H-F}$=48 Hz), 5.65 (3H, m).

(B) 2.0 g of 1-fluoro-2-amino-4-pentene hydrochloride prepared as in step A above is neutralized using 10% sodium hydroxide, saturated with sodium chloride and extracted with diethylether. The ether extract is then dried and concentrated to afford 1-fluoro-2-amino-4-pentene. The latter is converted to 1-fluoro-2-amino-4-pentene hydrobromide by conventional treatment with a 40% (w/w) solution of hydrogen bromide in dioxane at 25°-28° C. for 30 to 60 minutes and then diluted with diethylether and collected.

EXAMPLE 3

1-Fluoro-2-Tert-Butoxycarbonylamino-4-Pentene

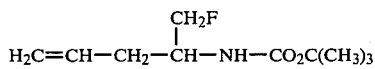

Tert-Butoxycarbonyloxyimino-2-phenylacetonitrile (3.34 g, 13.6 mmoles) in dry tetrahydrofuran (40 ml) is slowly added with ice cooling to a stirred mixture of 1-fluoro-2-amino-4pentene hydrochloride (1.9 g, 13.6 mmoles) prepared in Example 2 and triethylamine (2.78 g, 27.2 mmoles) in tetrahydrofuran (30 ml). After standing overnight (about 16 hours) at room temperature, water is added, the tetrahydrofuran is removed under reduced pressure, and the residue is extracted twice with ether. After washing with 1 N sodium hydroxide, then with water until neutral, the organic layer is dried and concentrated at reduced pressure to give 1-fluoro-2-tert-butoxycarbonylamino-4-pentene (2.33 g, 85%) as an oil which is used in Example 4 without further purification.

NMR ($CDCl_3$): δ1.43 (9H,s), 2.30 (2H, t, J=7 Hz), 3.67 (1H, m) 4.35 (2H, d of m, J=H-F=47 Hz), 5.47 (3H, m).

EXAMPLE 4

4-Fluoro-3-Tert-Butoxycarbonylamino-1-Butanoic Acid

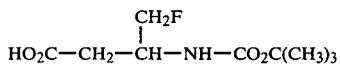

1-Fluoro-2-tert-butoxycarbonylamino-4-pentene (1.02 g, 5 mmoles) prepared in Example 3, dissolved in glacial acetic acid (15 ml), is added to potassium permanganate (2.37 g, 15 mmoles) in water (75 ml), and kept overnight (about 16 hours) at room temperature. After destroying the excess of permanganate with 10% sodium bisulfite solution and saturating with sodium chloride, the mixture is extracted twice with ether. Evaporation gives 4-fluoro-3-tert-butoxycaronylamino-1-butanoic acid (776 mg) as a white solid which on recrystallization from diethylether by addition of petroleum ether affords 676 mg (61%) of pure 4-fluoro-3-tert-butoxycarbonylamino-1-butanoic acid, m.p. 112°-112.5° C.

Anal. Calcd. for $C_9H_{16}O_4NF$: C, 48.86; H, 7.29; N, 6.33; Found: C, 48.91; H, 7.16; N, 5.99.

NMR ($CDCl_3$): δ1.43 (9H, s), 2.65 (2H, d, J=6 Hz), 4.21 (1H, m), 4.45 (2H, d of m, $J_{H-F}$=47 Hz).

EXAMPLE 5

4-Fluoro-3-Amino-1-Butanoic Acid

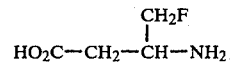

(A) 4-Fluoro-3-tert-butoxycarbonylamino-1-butanoic acid (545 mg, 2.46 mmoles) is dissolved in dry ether (20 ml) saturated with hydrogen chloride gas. After a few minutes, the solution becomes turbid and white crystals start to precipitate. Recrystallization from ethanol by addition of diethylether affords 4-fluoro-3-amino-1-butanoic acid hydrochloride (265 mg, 68%), m.p. 152°-153° C. (dec).

Anal. Calcd. for $C_4H_9O_2NFCl$: C, 30.49; H, 5.76; N, 8.89; Found: C, 30.48; H, 5.73; N, 8.88.

NMR ($DCl/D_2O$, 6 N): δ3.00 (2H, d, J=7 Hz), 4.10 (1H, m), 4.83 (2H, d of m, $J_{H-F}$=46 Hz).

(B) 4-Fluoro-3-amino-1-butanoic acid hydrochloride prepared as in step A above is dissolved in ethanol and an equimolar amount of triethylamine is added. The resultant solution is allowed to stand overnight (about 16 hours) at 4° C. and then the precipitate is filtered off and recrystallized from water by addition of ethanol to yield free 4-fluoro-3-amino-1-butanoic acid.

EXAMPLE 6

Vinyl Monofluoromethyl Ketimine Magnesium Bromide

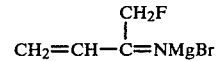

Vinyl monofluoromethyl ketimine magnesium bromide is prepared by substantially the procedure described in Example 1 from vinyl bromide and fluoroacetonitrile using tetrahydrofuran as the solvent.

EXAMPLE 7

1-Fluoro-2-Amino-3-Butene Hydrochloride

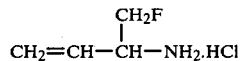

The procedure of Example 2 is substantially repeated commencing from the ketimine salt product of Example 6 to yield an oily precipitate (11.4 g, 48%) of 1-fluoro-2-amino-3-butene hydrochloride.

NMR ($D_2O/DCl$; std TMS): δ4.37 (1H, m) 4.80 (2H, d of m, $J_{H-F}$=44 Hz), 5.83 (3H, m).

EXAMPLE 8

1-Fluoro-2-Tert-Butoxycarbonylamino-3-Butene

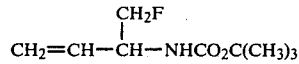

The procedure of Example 3 is substantially repeated commencing from the 1-fluoro-2-amino-3-butene hydrochloride product of Example 7 to yield 1-fluoro-2-tert-butoxycarbonylamino-3-butene (11.4 g; 68.5%).

NMR (CDCl₃): δ1.47 (9H, s), 4.37 (1H, m), 4.40 (2H, d of m, $J_{H-F}=48$ Hz), 5.57 (3H, m).

EXAMPLE 9

1-Fluoro-2-Tert-Butoxycarbonylamino-3-Propionic Acid

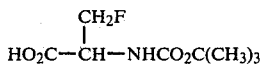

1-Fluoro-2-t-butoxycarbonylamino-3-butene (740 mg, 3.9 mmoles) prepared in Example 8 is oxidized with potassium permanganate and subsequently worked up substantially as described in Example 4 to yield, after evaporation, 1-fluoro-2-t-butoxycarbonylamino-3-propionic acid (530 mg, 66%) as an oil containing some impurities (from NMR).

EXAMPLE 10

1-Fluoro-2-Amino-3-Propionic Acid (i.e. β-Fluoroalanine)

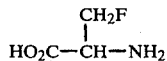

The t-butoxycarbonyl derivative prepared in Example 9 (530 mg, 2.58 mmoles) dissolved in 6 N hydrochloric acid (10 ml) and glacial acetic acid (3 ml) is kept at room temperature for 2 hours. The oil obtained by evaporation is dried under vacuum and dissolved in a few milliliters of dry ethanol. Treatment with sufficient triethylamine to neutralize the solution to pH 5 to 6 gives a precipitate (185 mg, 67%) which is recrystallized in water/ethanol (108 mg, m.p. 159° C.).

Anal. Calcd. for C₃H₆O₂NF: C, 33.65; H, 5.65; N, 13.06. Found: C, 33.75; H, 5.53; N, 12.93.

NMR (DCl 37%): δ4.68 (1H, d of broad sx, J=28 Hz), 5.07 (2H, d of m, $J_{H-F}=45$ Hz).

EXAMPLE 11

1-Fluoro-2-Deutero-2-Amino-3-Butene Hydrochloride

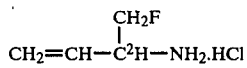

The procedure of Example 7 is repeated except that sodium borodeuteride (NaB²H₄) is used instead of sodium borohydride to yield 1-fluoro-2-deutero-2-amino-3-butene hydrochloride.

NMR (D₂O/DCl) δ4.77(2H, d of broad d, $J_{H-F}=45$ Hz), 5.82 (3H,m).

The product is optically resolved by fractional crystallization from ethanol of the D-tartrate salt (which is obtained by the procedure of step B of Example 2 using D-tartaric acid instead of hydrobromic acid) and addition of NaOH to free the D-configuration base.

EXAMPLE 12

1-Fluoro-2-Deutero-2-Tert-Butoxycarbonylamino-3-Butene

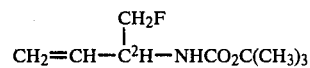

The procedure of Example 8 is repeated but using 1.8 g (14.2 mmole) D-1-fluoro-2-deutero-2-amino-3-butene hydrochloride prepared in Example 11, 3.50 g (14.2 mmole) BOC-ON and 2.87 g (28.4 mmole) triethylamine in 50 ml THF to yield D-1-Fluoro-2-deutero-2-tert-butoxycarbonylamino-3-butene as an oil (1.46 g, 54%).

NMR (CDCl₃) δ1.40 (9H, s), 4.30 (2,H, d, $J_{H-F}=46$ Hz), 5.43 (3H, broad m).

EXAMPLE 13

1-Fluoro-2-Deutero-2-Tert-Butoxycarbonyl-Amino-3-Propionic Acid

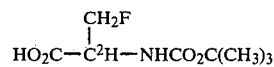

The procedure of Example 9 is repeated but using 1.46 g (7.7 mmole) 1-fluoro-2-deutero-2-tert-butoxycarbonylamino-3 butene prepared in Example 12, in 15 ml glacial acetic acid and 3.65 g (23.1 mmole) potassium permangate in 75 ml water to yield D-1-fluoro-2-deutero-2-tert-butoxycarbonyl-amino-3-propionic acid as a oil (1.1 g, 69%)

NMR (CDCl₃) δ1.43 (9H, s), 4.45 (2H, d of AB, $J_{H-F}=46$ Hz, $J_{A-B}=12$ H₂) 5.52 (1H, broad s), 11.57 (1H, broad s)

EXAMPLE 14

1-Fluoro-2-Deutero-2-Amino-3-Propionic Acid (i.e. β-Deutero-β-Fluoroalanine)

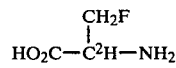

The procedure of Example 10 is repeated but using 1.0 g (4.8 mmole) 1-fluoro-2-deutero-2-tert-butoxycarbonyl-amino-3-propionic acid prepared in Example 13, in 25 ml ether saturated with hydrogen chloride gas to yield D-1-fluoro-2-deutero-2-amino-3-propionic acid as white crystals (140 g, 27%); mp 165.5° C.

NMR (D₂O/DCl) 5.00 (d of AB, $J_{H-F}=45$ Hz, $J_{A-B}=12$ Hz).

EXAMPLE 15

1-Fluoro-2-deutero-2-amino-3-propionic acid

The procedure of Example 10 is repeated using D,L-1-fluoro-2-deutero-2-tert-butoxycarbonyl amino-3-propionic acid (obtained by the procedures of Examples 11 to 13 but without the resolution step of Example 11) to yield D,L-1-fluoro-2-deutero-2-amino-3-propionic acid.

The optical isomers are separated by preferred recrystallization of the benzenesulfonate salts using the method of Dolling et al (J. Org. Chem. 1978, 1634–1640). Alternatively, chemical resolution of carbobenzoxy-β-deutero-β-fluoroalanine with quinine can be used as also described by Dolling et al (supra)

EXAMPLE 16

1-Fluoro-2-deutero-2-amino-3-butene hydrochloride

Under an atmosphere of nitrogen, vinyl magnesium bromide is prepared from 972 mg of magnesium turnings (40 mmoles), vinyl bromide (4.28 g, 40 mmoles) and 40 ml of dry tetrahydrofuran (THF). Once all the magnesium has reacted after heating for 2 hours at 60° C., the solution is cooled to −30° C., fluoroacetonitrile (2.36 g, 40 mmoles) in THF (20 ml) is added dropwise during 5 min and the reaction mixture is kept at −30° C. for an additional 30 min. A solution/suspension of sodium borodeuteride (98%) (1.67 g, 40 mmoles) in O-deuterated methanol ($CH_3OD$, 100 ml) and heavy water ($D_2O$, 2 ml) cooled to −50° C. is poured into the reaction mixture previously cooled to −50° C. The temperature rises to −25° C. and is allowed to rise to 0° C. over 1.5 hours. The mixture is acidified with 6 N HCl and evaporated. The residue is diluted with water, extracted twice with ether to remove by-products, made alkaline with 4 N NaOH, saturated with NaCl and extracted again twice with diethylether. After drying over $Na_2SO_4$, dry HCl gas is bubbled through the etheral solution; the NMR and MS data of the crystals obtained (1.98 g, 39%) is in accordance with 1-fluoro-2-deutero-2-amino-3-butene, hydrochloride. The product contains 2% of the nondeuterated analogue, which amount corresponds to the $H^1$-content of the sodium borodeuteride.

NMR ($D_2O$/DCl; std TMS); δ4.77 (2H, d of broad d, $J_{H-F}$=45 Hz, 5.82 (3H,m).

MS: no $M^+$, $M^+$ -33 (-$CH_2F$)=56 for 1-fluoro-2-deutero-2-amino-3-butene, hydrochloride: no $M^+$, $M^+$ -33 (-$CH_2F$)=57 for 1-fluoro-2-amino-3-butene, hydrochloride.

We claim:

1. A fluorinated alkenylamine of the formula

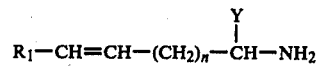

wherein
$R_1$ represents hydrogen or a straight or branched chain alkyl group of from 1 to 10 carbon atoms;
n represents zero, 1, 2, or 3; and
Y represents
(a), when n represents 0, $CH_2F$,
(b), when n represents 1, $CH_2F$ or $CHF_2$, and
(c), when n represents 2 or 3, $CH_2F$, $CHF_2$, or $CF_3$,
or an acid addition salt thereof, or a derivative of said alkenylamine in which the amino group is protected against oxidation by a subsequently removable blocking group selected from lower alkanoyl, monocyclic aroyl, lower alkoxycarbonyl, carbobenzoxy, benzenesulfonyl, tosyl, and phthalyl.

2. A compound as claimed in claim 1 wherein $R_1$ represents hydrogen or methyl.

3. A compound as claimed in claim 2 wherein $R_1$ represents hydrogen and n represents 1.

4. 1-Fluoro-2-amino-3-butene as claimed in claim 2 having the formula

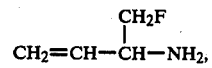

or an acid addition salt thereof, or a derivative of said aminobutene in which the amino group is protected against oxidation by a subsequently removable blocking group selected from lower alkanoyl, monocyclic aroyl, lower alkoxycarbonyl, carbobenzoxy, benzenesulfonyl, tosyl, and phthalyl.

5. A compound as claimed in claim 1 wherein the hydrogen atom on the α-carbon atom relative to the amino group is a deuterium atom.

* * * * *